United States Patent [19]

Gregory et al.

[11] 4,370,611

[45] Jan. 25, 1983

[54] IDENTIFICATION OF MATERIALS USING THEIR COMPLEX DIELECTRIC RESPONSE

[75] Inventors: William D. Gregory, Vienna; Luigi Morelli, Sterling, both of Va.

[73] Assignee: Georgetown University, Washington, D.C.

[21] Appl. No.: 28,452

[22] Filed: Apr. 9, 1979

Related U.S. Application Data

[63] Continuation of Ser. No. 847,425, Nov. 1, 1977, abandoned.

[51] Int. Cl.³ .............................................. G01R 27/26
[52] U.S. Cl. .............................. 324/61 R; 324/57 SS; 324/61 QS; 324/65 R
[58] Field of Search ............. 324/61 R, 61 QS, 65 R, 324/57 SS; 340/500; 86/1 B

[56] References Cited

U.S. PATENT DOCUMENTS

| | | | |
|---|---|---|---|
| 3,155,898 | 11/1964 | Chope | 324/61 X |
| 3,255,412 | 6/1966 | Liu | 324/61 R |
| 3,479,585 | 11/1969 | Liebel et al. | 324/57 SS |
| 3,739,267 | 6/1973 | Bart | 324/61 R X |
| 3,746,975 | 7/1973 | Maltby | 324/61 R X |
| 3,774,237 | 11/1973 | Hardway, Jr. | 324/61 R |
| 3,774,238 | 11/1973 | Hardway, Jr. | 324/61 R |
| 3,860,882 | 1/1975 | Maltby et al. | 330/291 |
| 3,864,626 | 2/1975 | MacLean et al. | 324/61 R |
| 4,058,766 | 11/1977 | Vogel et al. | 324/61 R |
| 4,181,881 | 1/1980 | Preikschat | 324/61 R |

FOREIGN PATENT DOCUMENTS 1448010 1/1969 Fed. Rep. of Germany .

Primary Examiner—Stanley T. Krawczewicz
Attorney, Agent, or Firm—John J. Byrne

[57] ABSTRACT

The non-linear conductance and capacitance characteristics of electrically non-homogenous materials over a given frequency range are used to identify and analyze such materials.

12 Claims, 8 Drawing Figures

IDENTIFICATION OF MATERIALS USING THEIR COMPLEX DIELECTRIC RESPONSE

This is a continuation application of Ser. No. 847,425, filed Nov. 1, 1977, now abandoned.

BACKGROUND OF INVENTION

This invention relates to testing of materials, particularly materials which are non-homogenous.

These materials are mixtures of two or more component materials, each of which has a very different electrical conductivity and dielectric constant. Materials so composed, because of their electrical properties, are often termed non-homogenous. Some examples of these kinds of materials are explosives, which are composed of the explosive molecule with high dielectric constant and an inert filler such as sawdust which has a comparatively low dielectric constant; another example is the mixture of water and soil, which may appear uniform in consistency, yet water and soil have clearly different electrical characteristics.

Further examples are water and suspended solids or even marbleized meat where the component elements in this case are lean muscle tissue and fatty tissue.

There has been a long-standing need for a rapid non-destructive test of non-homogenous materials that will readily identify them or give their properties. Two immediate applications for such tests are in the field of letter bomb detection and in soil analysis.

With respect to security detection, the ability to package explosives in small envelopes, and mail them through the mail has presented a long-standing security problem. With respect to soil analysis, there is a need for a rapid soil test in the field, which will give information regarding moisture content or mechanical properties.

It has been found that both of these materials have distinct conductive characteristics which are non-linear over given frequency ranges. This information can be used to identify and analyze such materials.

SUMMARY AND FEATURES OF INVENTION

Accordingly, this invention is directed to providing a non-destructive test for non-homogenous materials, a constituent of which has a high dielectric property.

It further provides an electronic test apparatus wherein the electrical properties of the material are used to give information with regard to its type and composition.

A feature of this invention is the use of the conductive properties of non-homogenous materials to provide a means for testing.

A still further feature of this invention is the ability to test materials in a closed container.

Another feature of this invention is the provision of a testing capability which will identify explosives in packages such as letters.

A still further feature of this invention is to provide a testing technique which gives almost instantaneous readings and permits scanning of many objects at a very high rate.

Another feature of this device is the use of conductive curve data based on frequency response to distinguish non-homogenous types of material having high dielectric elements from other types of material.

Another feature of this invention is the use of conductive level response and slope of the conductive curve to distinguish various types of material, and to give information on concentration of the high dielectric element within the composition.

A still further feature of this invention is to provide apparatus which will permit determination of the moisture content in non-homogenous materials, such as soils.

DESCRIPTION OF THE INVENTION

Figure 1:
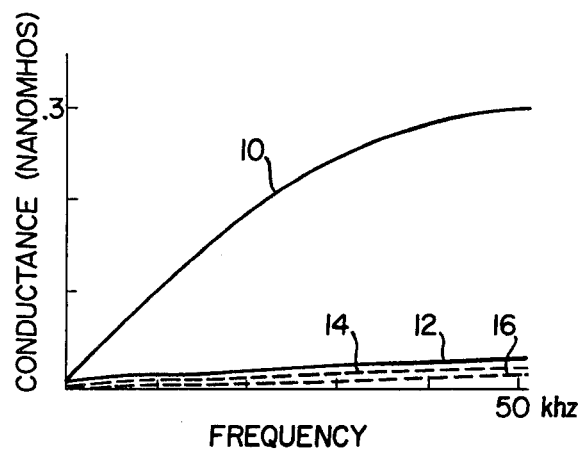
FIG. 1 shows conductance versus frequency curves and illustrates the conductance response of several explosives as compared to other materials.
Figure 2:
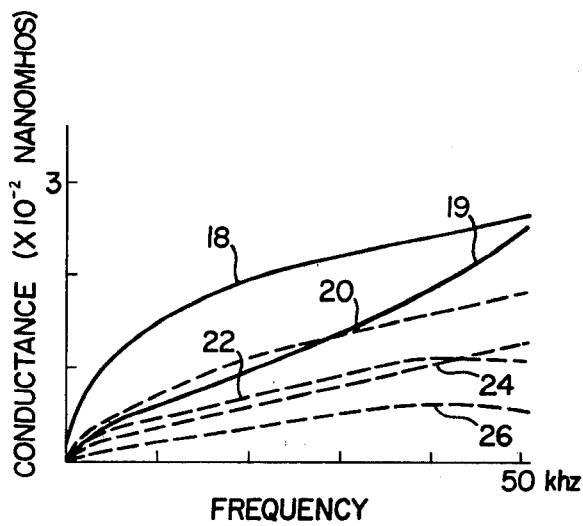
FIG. 2 is a plot of conductance versus frequency for several explosives and non-explosive material which illustrates the higher conductance level for explosives.

Referring particularly to the drawings, FIGS. 1 and 2 show conductance versus frequency curves for envelopes containing explosives and non-explosive materials. The curves were obtained by placing the envelope between two flat spaced plates which form a capacitive element and are part of a conductance sensitive electronic circuit.

In FIG. 1, the curve 10 is for the explosive compound PETN and shows a capacitive value for frequencies to fifty kilohertz. Note that the conductance rises sharply for PETN to a value of 0.3 nanohms at which point it levels out.

The solid line 14 is for an envelope containing the explosive Compound C which has a higher conductance level than the two dashed lines which are respectively the curves for envelopes containing plexiglass and paper.

FIG. 2 also shows conductance vs. frequency curves for explosive substances as a solid curve and non-explosive substances as dashed curves. It will be noted that the conductance values on this graph are tenfold greater than those of the curves in FIG. 1. This scale clearly shows the higher conductive level for the explosive Compound C shown in line 18, and for dynamite 19. Curve 20 is for plexiglass within an envelope and is lower than curves 18 and 19. Curve 22 has a lower conductance yet, and is obtained for an envelope which contains both paper and coins. Curve 24 is the curve for a plain envelope with paper, and curve 26 is obtained for an envelope which contains paper and two credit cards.

These figures show the large conductance change of explosive materials as a function of frequency, particularly with respect to PETN and dynamite. With respect to Compound C, it will also be noted that there is a large conductance change with frequency for this material in the lower frequency range as illustrated in FIG. 2.

On the contrary, non-explosive substances show a much lower change in conductance for change in frequency.

The explosive materials are a mixture of a binder with an explosive. The explosive has very high dielectric properties and has a large non-linear loss component over a frequency range up to approximately fifteen kilohertz.

Figure 3:
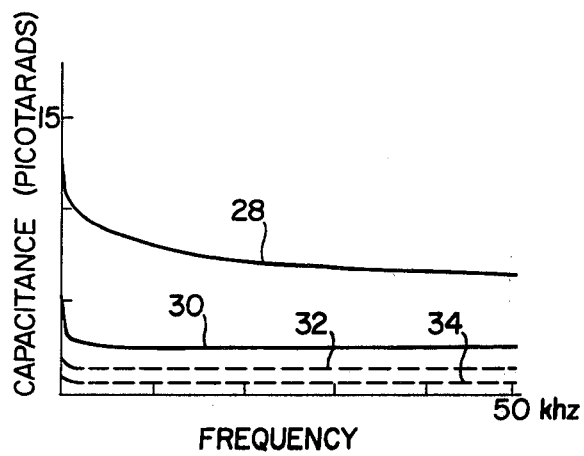
FIG. 3 is a capacitance versus frequency diagram showing curves for several explosives and non-explosives.

The capacitive values are proportional to the permitivity of the sample inserted between the plates. As seen in FIG. 3, the plots of capacitance versus frequency from approximately one hundred hertz to fifty kilohertz shows that the explosives shown in solid line have a permitivity which has some frequency dependence, and that the capacitance is much larger in value than that for non-explosive samples shown in dotted outline. The curve for the explosive PETN is shown at 28, and the curve for Compound C is shown at 30. Curves 32 and 34 respectively show the results obtained for envelopes containing plexiglass alone and for an envelope containing two credit cards.

Figure 4:
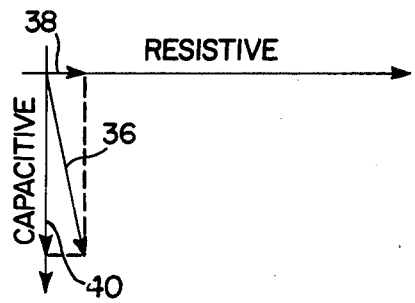
FIG. 4 is a vector diagram for a typical capacitive component which shows both the capacitive and resistive components, both of which are of interest.

The significance of this property of non-homogenous materials having a high dielectric element is illustrated in FIG. 4. The electrical vector 36 representing the large loss across the plates of the capacitor has a capacitive component 40 and a resistive component 38. The capacitive component contains information with respect to the dielectric constant. The resistive component 38 provides basic information with respect to the resistive value of the loss. Different measurements are obtained for each frequency applied in a range from up to fifty kilohertz for a given sample which is placed between the plates of the capacitive element. With the resistive component a value can be found for the resistance at each frequency. The conductance is merely a reciprocal of this value.

Explosive materials have been found to have a non-linear conductance curve. They are a mixture of the unstable explosive compound having a high dielectric constant, and an inert filler such as sawdust which does not have such a property.

The conductance curve for each type of explosive is distinctive.

Figure 5:
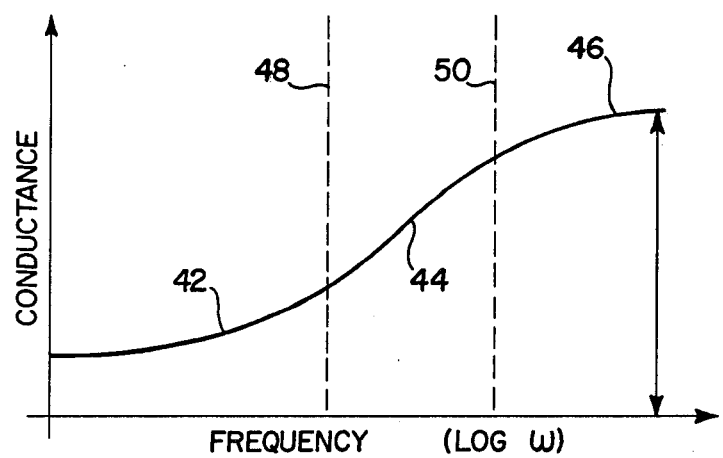
FIG. 5 is a graph of a typical curve for explosives showing the rate of change in the conductance curve with respect to concentration of explosives.

In FIG. 5, the variation in conductance as plotted against the log value of frequency produces a somewhat S-shaped curve. Factors which are of interest are the rate at which the conductance increases with frequency, and the point at which the conductance reaches a maximum. The rate of change of these curves is a function of the volume concentration of the high dielectric material (explosive) in the filler. The magnitude of the curve where the rate of change becomes zero is related to the amount of high dielectric property material, as well as its volume concentration.

The lower section of the curve 42 shown in FIG. 5 has a gradual rise to the middle portion 44 and a leveling out of the curve at 46. Midportion of the curve 44 between the dashed lines 48 and 50 shows the change of rate of conductance with frequency. This portion of the curve is related to the concentration of the dielectric element in the composition.

The leveling out point of the curve at the upper portion of 46 is related to both the volume concentration and the amount of material.

It has been found that each type of material has its own distinctive conductance curve, and therefore different types of material can be distinguished one from another after various sets of reference curves have been obtained. These distinctive conductance curves or signatures make it possible to scan a package such as an envelope without opening it, and to specifically identify both the amount and type of material within the envelope or package.

Figure 6:
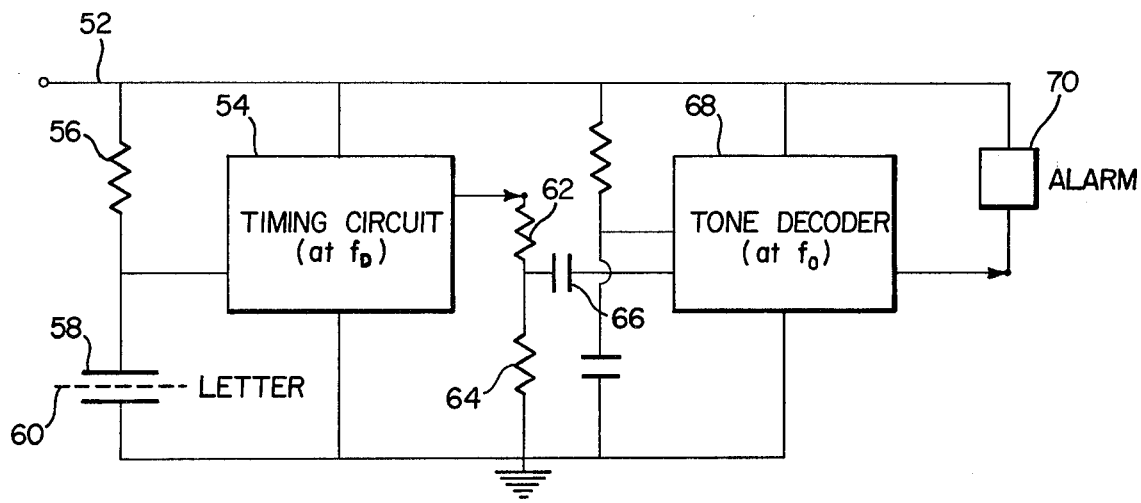
FIG. 6 illustrates a circuit for detecting change in conductance which uses a timing circuit and a tone decoder.

There are a number of different electrical circuits that can be used to take advantage of the conductive characteristics of the non-homogenous dielectric containing materials. One such circuit is shown in FIG. 6. This circuit is expressly directed toward examining letters for those that might contain explosives.

An input line 52 is connected in parallel to a timing circuit 54 and with a line containing a resistance 56 and a capacitive element 58. This type of circuit is well-known and an example of such a circuit can be found in the "Linear Data Book", National Semiconductor, 1976, Component LM555. The capacitive element 58 consists of two parallel spaced plates between which a closed letter 60 is passed.

The R-C circuit formed by the resistance 56 and the capacitive element 58 affect the timing circuit 54 when there is a change in value of the capacitive element 58. The introduction of a letter 60 containing a high dielectric material does this. Inasmuch as the capacitive element does not represent a pure conductance, the equivalent circuit of this element is a capacitance in parallel with a resistor. The voltage component would be essentially as shown in FIG. 4, in which the dominant term for the vector is the capacitive component.

The explosive causes a large change in the conductive value and therefore changes the frequency output of the timing circuit 54. When the plates of capacitive element 58 do not have an object between them the timer frequency is a certain given value. This output is fed through the resistive network 62 and 64 and is coupled through capacitor 66 to the tone decoder. The tone decoder 68 is a well-known circuit. A specific example can be found in the "Linear Data Book", National Semiconductor, 1976, Component LM567. The tone decoder is tuned to this frequency which is represented as $f_o$. When the two frequencies are in tune the tone decoder output is high.

However, when a material containing a high dielectric type substance (explosive) is inserted between the plates, the capacitance of the element 58 changes. This is because of the change in permitivity caused by the high dielectric material. Therefore, since the equivalent circuit represents a capacitance and resistance in parallel, vector measurements to determine both the capacitive and resistive components (FIG. 4) are of interest. The accurate measurement of the resistive component, which is the reciprocal of conductance will give a conductance value.

Since the charging time for the capacitive element 58 of the R-C network of the timing circuit changes, the output of the timing circuit changes also. The magnitude of this difference is large enough to exceed the band width of the tone decoder. The tone decoder output consequently is lowered, and the alarm circuit 70 which is made to sense such changes is activated. Many different types of alarm systems are available and can be used. For example, this could be a sona alert, LED (light emitting diode) and incandescent lamp, or a bell alarm. The only requirement is that the alarm device respond appropriately to the voltage state leaving the tone decoder 68, when the letter 60 is between the plates of the pick-up assembly.

The values can be selected so that the sensitivity of the circuit can be changed to suit the items being scanned. The given circuit can readily be varied if desired by varying the band width of the decoder 68.

The frequency applied to the circuit through line 52 will be between thirty to fifty kilohertz for explosives. This can be seen by referring to FIGS. 1 to 3, the higher conductive and capacitive reaction of explosives is readily distinguishable.

The circuit is also fast acting. For example, when it is used as a letter bomb detector on the order of from 700 to 1000 pieces can be scanned per minute.

If identification of the explosive were required, a signature curve would have to be generated by applying a plural number of frequencies. The simple letter bomb detector operates on a single frequency in which the conductance level or capacitance change (loss) is used to determine presence of any explosive since all conductance readings will be high.

Construction of the plates of the capacitive element 58 when used as a letter bomb detector can be almost envelope size. The plates used were thin metal three inches wide and eleven inches long and were parallel spaced about half an inch apart.

The phase angle of the frequency applied to the circuit with reference to the frequency applied across the capacitive element 58 is also of importance. They should be within one-half a degree of being in phase or be corrected for such situation in order to get good accurate readings. It is further essential that a very stable fixed oscillator signal be used to get clear accurate readings.

Figure 7:
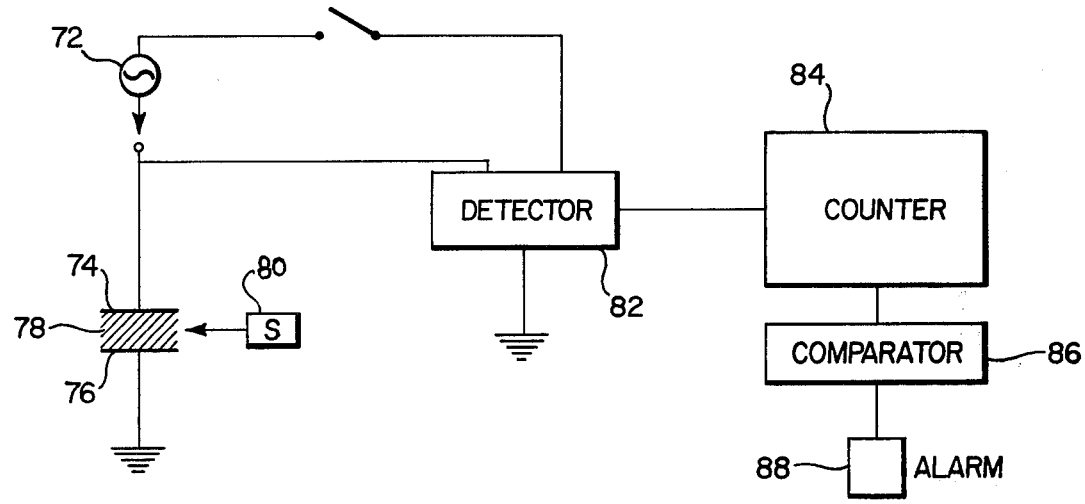
FIG. 7 illustrates another type of circuit that can determine change in conductance and which uses a detector and a counter circuit.

Another circuit arrangement is shown in FIG. 7 for detecting high dielectric bearing substances. The periodic frequency generating source 72 is connected across a capacitive element having spaced plates 74,76 which have an air gap 78 between them. The sample 80 generally indicated at S is moved between the plates and the change in capacitance will be picked up in the detector 82. An example of a detector circuit that would be useful would be any voltage comparator such as those described in the "Linear Data Book", National Semiconductor, 1976, which are appropriately configured to yield timing information. Ordinarily, the current is allowed to charge the capacitive plates 74,76 until the voltage drop across them exceeds a preselected amount. At that time the detector cuts off the current such that the charge between the plates decays to a given level which then causes the detector to connect the current source back into the line to recharge the capacitor. With this arrangement the detector acts as a periodic voltage generator giving a signal the period of which is dependent upon the charging and discharging of the capacitive element. When the sample is inserted between the plates 74 and 76 the capacitance of the element is changed, and this in turn changes the output signal from the detector circuit 82 to the counter 84. The counter 84 supplies a signal to the comparator 86, and if this difference is sufficiently large the comparator will pass a signal to the alarm circuit 88 which will be activated. Examples of a counter 84 and a comparator 86 can be found in the "TTL Data Book", National Semiconductor, Feb. 1976, or in "CMOS Integrated Circuits", Solid State Scientific Inc., Nov. 1976.

The circuit is a fast acting circuit which is simple to construct. The drawback is that since the time constant of the capacitor is the product of both the resistance and capacitive elements, these component values cannot be readily determined.

Figure 8:
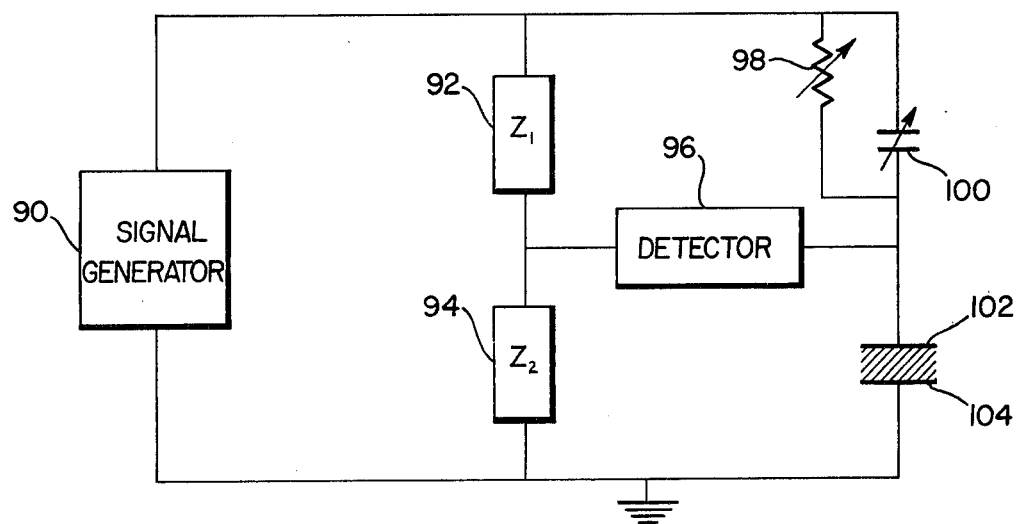
FIG. 8 is a block diagram of a bridge circuit which can be used to determine conductance change.

FIG. 8 shows the bridge circuit which is driven by a sine wave generator. Bridge elements 92 and 94 are balanced impedances which are connected by a detector 96. The detector 96 can include any heterodyning lock-in such as an ITHACO, Dynatrac 3, or a PAR, Model 5202, or a multiple phase sensitive detector, such as shown in Evans Associates catalog of phase shift and phase detector boards, or a digital computer with analog to digital converter and sample and whole amplifier. The detector will be nulled when the bridge is balanced. Variable resistance 98 and variable capacitor 100 match impedances Z1 shown as element 92. They also represent the equivalent circuit of the capacitive element in the remaining arm of the bridge formed by the parallel spaced plates 102 and 104.

The variable elements 98 and 100 effectively control the null position of the detector 96. A sample placed between the plates 102 and 104 can unbalance the bridge and rebalance is then obtained by adjusting elements 98 and 100. The adjustment gives the resistive and capacitive values introduced by the sample.

Again, it should be noted that some attention must be paid to the in-phase relationship of the applied periodic voltage. This circuit will be effective in obtaining signatures at various frequencies for the different types of explosive materials when identification is required. However, it should be noted that where frequencies are applied sequentially so as to obtain signature data, time must be allowed for manual or other manner of adjustment of the variable resistor and capacitor to rebalance the bridge.

The circuit of FIG. 8 can also be used as a calibrated bridge detector circuit. A known sample is placed between the plates 102 and 104 and will unbalance the bridge voltage. The quadrature components of the voltage unbalance are recorded and these are compared to known capacitive and resistance changes due to the sample. If these values do not agree with known values then the known values along with recorded values are used as a set of calibration numbers to correct further voltage readings to reflect true resistance and capacitive component data.

The data obtained on conductance for the various frequencies for a given sample will provide a conductance signature which can be stored and then subsequently compared with an unknown sample which is placed between the capacitor plates 102 and 104.

The detector circuit may include either a vector voltmeter, an AC voltmeter, a phase sensitive detector, or a digital computer.

With respect to identifying the type of dielectric material or the explosive, it should be noted that a number of frequencies must be applied to the bridge to obtain active data and this can be compared with the stored signatures for the various types of materials previously obtained.

A computer is used to perform this function, inasmuch as there is a requirement for storage of the sequentially obtained data numbers at each frequency and comparing them with the previously stored data. The technique can either use a comparative approach, or could very readily be adapted to a signal level or signal characteristic approach.

With respect to the system, it has also been found that data can be obtained which will give the location of an explosive in a package merely by observing and changing capacitance and conductance of the package as it passes between the plates. A reference point such as velocity of the envelope in its lateral passage or a time base can be used to sense the point at which the capacitive or conductance values change. With correlation of this data, the position of the explosive in the envelope or package can readily be determined.

A number of applications of this technique and circuitry include quality control in manufacturing processes, soil analysis for water concentration, analysis of tissue for fat concentration, and amount of contaminants in a fluid. In the latter instance, there is a possibility of determining the amount of oil, sludge, or foreign materials in a water sample. It is also possible to monitor and check for drugs, such as heroin and cocaine in a package.

While this invention has been described, it will be understood that it is capable of further modification, uses and/or adaptations of the invention following in general the principles of the invention and including such departures from the present disclosure as come within known or customary practice in the art to which the invention pertains, and as may be applied to the essential features hereinbefore set forth, as fall within the scope of the invention or the limits of the appended claims.

What we claim is:

1. Method for identifying material having frequency responsive dielectric and conductive properties, said method comprising:
   (a) providing a capacitive system for producing an output signal and for producing a change in output signal when a material to be identified is brought within the influence of said capacitive system, said output signal having a value reflective of the dielectric and conductive properties of said material, said capacitive system including at least one capacitive element;
   (b) establishing a reference value of an output signal of said capacitive system in the absence of any material to be identified in said system, said output signal being with reference to a plurality of frequencies applied to said system, each of said plural frequencies being pre-selected so that output signal has a value reflective of said dielectric and conductive properties when said material is brought within the influence of said system;
   (c) introducing the material to be identified into the influence of said capacitive system and subjecting said material to said plurality of frequencies to produce an output signal having a value reflective of the dielectric and conductive properties of said material;
   (d) resolving said output signal into separate resolved components including a resolved capacitive component and a resolved conductive component, for each of said plural pre-selected frequencies, each of said resolved capacitive and conductive components having a value reflective of said dielectric and conductive properties of said material;
   (e) identifying said material by determining the change in value of at least one of said resolved capacitive and conductive components for each of said plural pre-selected frequencies from the reference value of said output signal to the value obtained when said material is brought within the influence of said capacitive system, to give at least one set of material identification data corresponding to at least one of said resolved capacitive and conductive components at each of said plural pre-selected frequencies, said at least one set of material identification data corresponding to said dielectric and conductive properties of said material, and using at least one of said sets to identify said material.

2. Method according to claim 1 wherein said plurality of pre-selected frequencies is applied sequentially to said capacitive system to produce said output signal.

3. Method according to claim 1 wherein said plurality of frequencies is applied simultaneously to said capacitive system to produce an output signal.

4. Method according to claim 1 wherein said at least one set of material identification data is in the form of a signature representative of said material, said material being identified by comparing said signature with that obtained by bringing a reference sample of said material to be identified within the influence of said capacitive means.

5. Method according to claim 1 wherein said material identification data corresponding to said resolved conductive components is used to identify said material.

6. Method according to claim 1 wherein said material identification data corresponding to said resolved capacitive components is used to identify said material.

7. Method according to claim 1 wherein said plurality of frequencies ranges between 10 hertz and 150 kilohertz.

8. Method according to claim 1 wherein said plurality of frequencies ranges between 20 and 150 kilohertz.

9. Apparatus for identifying material having frequency responsive dielectric and conductive properties, comprising:
   (a) capacitive means for producing an output signal and for producing a change in output signal when a material to be identified is brought within the influence of said capacitive means, said output signal having a value reflective of the dielectric and conductive properties of said material, said capacitive means including at least one capacitive element;
   (b) frequency generating means connected to said capacitive means for generating a plurality of frequencies, said plural frequencies being applied to said capacitive means and being pre-selected so that said output signal has a value reflective of said dielectric and conductive properties when said material is brought within the influence of said capacitive means;
   (c) measuring means connected to said capacitive means for resolving said output signal into separate resolved components including a resolved capacitive component and a resolved conductive component for each of said plural pre-selected frequencies, and for determining the change in value of at least one of said resolved capacitive and conductive components for each of said plural pre-selected frequencies from a reference value of said output signal established in the absence of said material from the influence of said capacitive means to a value obtained when said material is brought within the influence of said capacitive means, each of said resolved capacitive and conductive components being reflective of the dielectric and conductive properties of said material, whereby said material introduced into the influence of said capacitive means can be identified.

10. Apparatus according to claim 9 wherein said capacitive element includes at least two spaced-apart capacitive plates which are spaced sufficiently apart to permit said material to be identified to be brought within the influence of said capacitive element.

11. Apparatus for identifying material having frequency responsive dielectric and conductive properties, comprising:
  (a) capacitive means for producing an output signal and for producing a change in output signal when the material to be identified is brought within the influence of said capacitive means, said output signal having a value reflective of the dielectric and conductive properties of said material, said capacitive means including at least one capacitive element having at least two spaced apart capacitive plates;
  (b) frequency generating means connected to said capacitive means for generating a plurality of frequencies, said plural frequencies being applied to said capacitive means and being pre-selected so that said output signal has a value reflective of said dielectric and conductive properties when said material is brought within the influence of said capacitive means;
  (c) measuring means connected to said capacitive means for resolving said output signal into separate resolved components including a resolved capacitive component and a resolved conductive component for each of said plural pre-selected frequencies, and for determining a change in value of at least one of said resolved capacitive and conductive components for each of said plural pre-selected frequencies from a reference value of said output signal established in the absence of said material from the influence of said capacitive means to a value obtained when said material is brought within the influence of said capacitive means, each of said resolved capacitive and conductive components being reflective of the frequency responsive dielectric and conductive properties of said material, said measuring means including a balanceable bridge circuit having a detector connected parallel therewith, said capacitive means being contained in one arm of said balanceable bridge, and a variable resistance and variable capacitance being contained in the other arm of said bridge circuit, whereby said material brought within the influence of said capacitive means can be identified.

12. Apparatus for identifying material having frequency responsive dielectric and conductive properties, comprising:
  (a) capacitive means for producing an output signal and for producing a change in output signal when a material to be identified is brought within the influence of said capacitive means, said output signal having a value reflective of the dielectric and conductive properties of said material, said capacitive means including at least one capacitive element having at least two spaced-apart capacitive plates;
  (b) frequency generating means connected to said capacitive means for generating a plurality of frequencies, said plural frequencies being applied to said capacitive means and being pre-selected so that said output signal has the value reflective of said dielectric and conductive properties when said material is brought within the influence of said capacitive means, said frequency generating means generating a capacitive charge between said plates which decays over a certain charge decay time period, said change in output signal when a material to be identified is brought within the influence of said capacitive plates producing a change in said charge decay time period;
  (c) measuring means connected to said capacitive means for resolving said output signal into separate resolved components including a resolved capacitive component and a resolved conductive component for each of said plural pre-selected frequencies, and for determining the change in value of at least one of said resolved capacitive and conductive components for each of said plural pre-selected frequencies from a reference value of said charged decay time period established in the absence of said material from the influence of said capacitive means to a value of said charge decay time period obtained when said material is brought within the influence of said capacitive means, each of said resolved capacitive and conductive components being reflective of the frequency responsive of dielectric and conductive properties of said material, whereby said material brought within the influence of said capacitive means can be identified.

* * * * *